United States Patent [19]

Reszka

[11] Patent Number: 5,888,821
[45] Date of Patent: Mar. 30, 1999

[54] CHOLESTEROL DERIVATIVE FOR LIPOSOMAL GENE TRANSFER

[75] Inventor: Regina Reszka, Schwanebeck, Germany

[73] Assignee: Max-Delbrück-Centrum für Molekulare Medizin, Berlin, Germany

[21] Appl. No.: 700,446

[22] PCT Filed: Dec. 28, 1995

[86] PCT No.: PCT/DE95/01879

§ 371 Date: Dec. 13, 1996

§ 102(e) Date: Dec. 13, 1996

[87] PCT Pub. No.: WO96/20208

PCT Pub. Date: Jul. 4, 1996

[30] Foreign Application Priority Data

Dec. 28, 1994 [DE] Germany ......................... 44 46 937.3

[51] Int. Cl.$^6$ ........................... C12N 15/87; C12N 15/63; C12P 33/00
[52] U.S. Cl. .............................. 435/458; 435/52; 514/44; 514/12; 564/463; 536/23.1; 424/1.45; 424/450; 604/101
[58] Field of Search ............................. 604/101; 435/52; 424/1.45, 450; 536/23.1; 514/44, 12; 564/463

[56] References Cited

U.S. PATENT DOCUMENTS

| | | | |
|---|---|---|---|
| 4,084,010 | 4/1978 | Takemoto et al. | 426/458 |
| 5,260,290 | 11/1993 | De Luca et al. | 514/167 |
| 5,283,185 | 2/1994 | Epand et al. | 435/458 |
| 5,328,470 | 7/1994 | Nabel et al. | 604/101 |

OTHER PUBLICATIONS

Pinnaduwage, P., et al; Use of a Quaternary Ammonium Detergent in Liposome Mediated DNA Transfection of Mouse L–cells; Biochimica et Boiphysica Acta, 985 (1989) pp. 33–37.

Gao, Ziang, et al; A Novel Cationic Liposome Reagent for Efficient Transfection of Mammalian Cells; Biochemical and Biophysical Research Communications; vol. 179, No. 1, 1991; pp. 280–285.

Sigma Catalog, 1990, "Biochemicals Organic Compounds", St. Louis, MO, p. 419.

*Primary Examiner*—Christopher S. F. Low
*Attorney, Agent, or Firm*—Londa and Traub LLP

[57] ABSTRACT

The invention relates to a new cholesterol derivative for liposomal gene transfer. Areas of application of the invention are medicine and genetic engineering.

The new cholesterol derivative, 3β(N-(N,N'-dimethylaminoethane)-carbamoyl) cholesterol (DAC-Chol) is prepared by the reaction between N,N'- dimethylethylenediamine and chloroformyl cholesterol in equimolar mounts and purified by chromatography.

DAC-Chol is nontoxic and can be used advantageously for the in vivo direct liposomal gene transfer.

The object of the invention furthermore is a new method for the direct, in vivo liposomal gene transfer, which is characterized in that the liposomes/DNA complexes are applied continuously or repeatedly at selected time intervals by means of automatic or refillable pumping systems.

4 Claims, No Drawings

CHOLESTEROL DERIVATIVE FOR LIPOSOMAL GENE TRANSFER

This application is a filing under 35 U.S.C. 371 of PCT/DE 95/01879 filed 28 Dec. 1995.

The invention relates to a new cholesterol derivative for liposomal gene transfer. Medicine and genetic engineering are areas of application of the invention.

Cationic liposomes are effective, nonviral transfection reagents for animal cells in vitro (P. Felgner, G. Ringold, Nature 337/1989/, 387–388). The first reagent of this type, DOTMA (N-(1-(2,3-dioleyloxy)propyl)-N,N,N-trimethyl-ammonium chloride), after being mixed with an equimolar amount of DOPE (dioleyl phosphatidyl ethanolamine), is able to transfect a series of mammalian cells in vitro and in vivo.

The synthesis of DOTMA proceeds over many steps with a relatively low yield. The conventional commercial material, lipofectin, which contains DOTMA and DOPE, furthermore is relatively expensive. Other cationic liposomal reagents with commercially accessible cationic amphiphiles have proven to be relatively toxic with respect to the treated cells (Pinnaduwage et al., Biochim. Biophys. Acta 285/1989/, 33–37).

X. Gao and L. Huang (Biochem. Biophys. Res. Comm. 179/1991/, 280–285) have described the cationic cholesterol derivative 3 β(N-(N',N'-dimethyl-aminoethane)-carbamoyl) cholesterol (DC-Chol). It can be prepared in one step and liposomes with this lipid transfect more efficiently and are less toxic than the lipofectin reagent with respect to the treated cells.

It is an object of the invention to find a new cationic lipid which, while having a transfection ability comparable to that of DC-Chol, is less toxic and, with that, particularly suitable for in vivo applications.

Using DAC-Chol, the new material has the advantage over previously used materials of not being toxic towards highly sensitive cells and of leading to successful transfections in vitro as well as in vivo. The use of the material is demonstrated on glioblastoma cells of the rat, which otherwise can be transfected only with a low effectiveness. Transfection rates are attained, which are up to ten times higher than those attained with the calcium phosphate precipitation technique (CPPT). This finding may well be attributable to a more compact formation of the DNA, a better contact between cells and liposome over the positive charges of the vesicles and to a higher stability with respect to the enzymes breaking down the DNA.

As a result, it can be used advantageously for the direct liposomal gene transfer. Accordingly, immunoliposomes, for example, can also be produced by coupling organ-specific or tissue-specific antibodies with addition of DAC-Chol/DOPE. By a prior incubation of the DNA, which is to be transfected, with nucleoproteins (such as HMG-1), an increased integration and expression of the foreign gene can be attained after encapsulation or association in DAC-Chol/DOPE liposomes. A further increase in the uptake (fusion) of the DAC-Chol liposomes is possible, if fusion proteins or inactivated viruses are reconstituted or associated in the liposomal membrane.

It is furthermore of advantage that these liposomes can be administered without toxicities or immune reactions worth mentioning over automatic or refillable pump systems for a direct in vivo gene transfer (intratumoral or organ-specific). With this method, which can also be employed for other liposomes, a transfection effectiveness is attained, which is much higher than that attained with retroviral or adenoviral in vivo methods. With that, tumor cells, which are in the process of proliferating to different extents at a particular time, can be transfected and killed.

The invention will be described in greater detail in the following by means of examples.

EXAMPLES

1. Preparation of 3β(N-(N',N'-dimethyl-aminoethane)-carbamoyl) cholesterol (DAC-Chol)

The symmetric form of dimethylethylenediamine is reacted by the method of Gao et al. (Biochem. Biophys. Res. Comm. 179; 280) with chloroformyl cholesterol. The oily product obtained is subjected to column chromatography (silica gel 60, with a 9:1 (vol/vol) mixture of trichloromethane and methanol as solvent). The DAC-Chol isolated, after thin-layer chromatographic purification with a 65:35 (vol/vol) mixture of trichloromethane and methanol as solvent, has an Rf value of 0.53–0.57.

For further use, DAC-Chol is mixed with DOPE in the ratio of 3:2.

2. Marker- and TNF-alpha gene transfer with cationic liposomes in comparison to the calcium phosphate precipitation technique (CPPT) in vitro The marker gene transfer leads to a transfection rate for cationic liposomes, which is four times higher than that achieved with the CPPT method. In comparison with the usual transfection methods (CPPT), the human cell lines N64 and N31 show a four-fold to ten-fold higher transfection rate when DAC-Chol/DOPE liposomes are used. However, when F98 gioblastoma cells from rats are used, only slight differences are observed. It is interesting that the inventive preparation is not toxic despite the high content of DAC-Chol/DOPE liposomes resulting from the DNA portion. This can be demonstrated by means of vitality tests (MTT) as well as by morphological parameters.

TABLE 1

Maximum Transfection Efficiency (from 3 Experiments), as a Percentage of the Cells Transfected ($5 \times 10^5$, 5 μg DNA (pBAG))

| Transfection Method | N31 Cells | N64 Cells | F98 Cells |
| --- | --- | --- | --- |
| DAC-Chol | 1.26 | 2.00 | 1.06 |
| Lipofectin | 0.40 | 1.10 | 2.05 |
| $Ca_3(PO_4)_2$ | 0.2 | 0.52 | 0.76 |

TABLE 2 hTNF Expression after Gene Transfer from F98 Cells

| Transfection Methods | TNF Activity ng/ml of $5 \times 10^4$ cells, 24 hours |
| --- | --- |
| $Ca_3(PO_4)_2$ | 1.81 ± 0.29 |
| DAC-Chol/DOPE | 1.76 ± 0.3 |
| Lipofectin | 1.76 ± 0.29 |

The results are the average of 4 experiments+the standard deviation. The t test for independent samples shows that the differences between the results of the 3 techniques are not significant.

The hTNF secretion after the transfer with the different methods lies between 1 and 2 ng/mL. The secreted amount of TNF-alpha brings about a clear inhibition of growth of F-98 cells within 5 days. The inhibition in growth is accompanies by morphological changes and cell death. F98 cells, which are transfected with vector alone (pWG29del3), do not express detectable amounts of TNF and proved to be intact morphologically.

3. The Stimulation of the TNF-alpha Expression from DAC-Chol Liposomes by Dexamethasone

TABLE 3

Dexamethasone-Stimulated Expression of hTNF in Transfected Cells

| | No. of the Cell Clone | Dexamethasone ($10^{-6}$M/5 h) | TNF Activity ng/ml $5 \times 10^5$/24 hours | × fold |
|---|---|---|---|---|
| Lipofectin | 10 | – | 2.03 | |
| | | + | 17.89 | 8.9 |
| DAC-Chol/DOPE | 5 | – | 1.12 | |
| | | + | 19.78 | 17.6 |
| Transfectam | 8 | – | 2.93 | |
| | | + | 15.34 | 5.3 |

Dexamethasone can increase the hTNF production in F98 cell clones, obtained after transfection with DAC-Chol liposomes, by up to 18-fold. Starting from the previous results, cationic DAC-Chol liposomes are selected for the in vivo marker gene transfer.

4. LacZ in vivo Gene Transfer with DAC-Chol/DOPE Liposomes

After the in vivo marker gene transfer by means of DAC-Chol liposomes in implanted rat tumors (F98, 6 μg of LacZ/10 μL of DAC-Chol/DOPE), it was possible to show that, during a direct gene transfer, these liposomes were able to transfect up to 3 cell layers around the injection plane (measured at a positive X-gal coloration). On the other hand, it was not possible to detect any coloration by endogenous β-galactosidase in normal brain tissue.

I claim:

1. A compound for effecting gene transfer with an improved transfection rate compared to 3β(N-(N,N-dimethylaminoethane)-carbamoyl) cholesterol and lower toxicity to sensitive cells, according to the formula 3β(N-(N,N'-dimethylaminoethane)-carbamoyl) cholesterol.

2. A method for the preparation of the compound 3β(N-(N,N'-dimethylaminoethane)-carbamoyl) cholesterol as set forth in claim 1, comprising reacting N,N'dimethylethylenediamine and chloroformyl cholesterol together in equimolar amounts to form 3β(N-(N,N'-dimethylaminoethane)-carbamoyl) cholesterol, and purifying the 3β(N-(N,N'-dimethylaminoethane)-carbamoyl) formed.

3. A composition comprising a mixture of the compound comprising 3β(N-(N,N'-dimethylaminoethane)-carbamoyl) cholesterol as set forth in claim 1, and dioleoyl phosphatidylethanolamine.

4. A method of in vitro gene transfer, comprising the steps of:

associating or encapsulating a chosen DNA in a liposome comprising 3β(N-(N,N'-dimethylaminoethane)-carbamoyl) cholesterol/dioleoyl phosphatidylethanolamine, as set forth in claim 3, to form a liposome/DNA complex, and administering the resulting liposome/DNA complex to a cell line to thereby effect transfer of the DNA to the cells of the cell line.

* * * * *

UNITED STATES PATENT AND TRADEMARK OFFICE
CERTIFICATE OF CORRECTION

PATENT NO. : 5,888,821
DATED : March 30, 1999
INVENTOR(S) : Regina Reszka

It is certified that errors appear in the above-identified patent and that said Letters Patent is hereby corrected as shown below:

In Column 2, line 7, "3β(N, N'-dimethyl-aminoethane)-carbamoyl)" should read --3β(N', N'-dimethyl-aminoethane)- carbamoyl)

Signed and Sealed this

Thirtieth Day of November, 1999

Attest:

Q. TODD DICKINSON

Attesting Officer

Acting Commissioner of Patents and Trademarks